United States Patent [19]
Smith

[11] Patent Number: 5,712,252
[45] Date of Patent: Jan. 27, 1998

[54] METHOD OF AUGMENTING SOFT TISSUE IN MAMMALS

[75] Inventor: Dean Preston Smith, Knoxville, Tenn.

[73] Assignee: The University of Tennessee Research Corporation, Knoxville, Tenn.

[21] Appl. No.: 611,613

[22] Filed: Mar. 8, 1996

[51] Int. Cl.$^6$ .............................. A61K 38/00; A61K 2/00
[52] U.S. Cl. ............................ 514/21; 424/423; 424/424
[58] Field of Search .............................. 514/21; 424/423, 424/424

[56] References Cited

U.S. PATENT DOCUMENTS

| | | |
|---|---|---|
| 4,140,537 | 2/1979 | Luck et al. |
| 4,424,208 | 1/1984 | Wallace et al. |
| 4,582,640 | 4/1986 | Smestad et al. |
| 5,358,935 | 10/1994 | Smith et al. |

OTHER PUBLICATIONS

SWRI Scientists Invent Injectable Biocompatible Protein Filler, Biotech Business, vol. 8, No. 10, Oct. 1, 1995.
Freedberg, I.M., "Keratin: A Journey of Three Decades," *The Journal of Dermatology*, 20:321–28 (1993).
Coulombe, P.A., "The Cellular and Molecular Biology of Keratins: Beginning a New Era," *Current Opinion in Cell Biology*, 5:17–29 (1993).
Steinert, P.M., "Structure, Function, and Dynamics of Keratin Intermediate Filaments," *The Journal of Investigative Dermatology*, 100(6):729–34 (1993).
Diokno, A.C., "Epidemiology and Psychosocial Aspects of Incontinence," *Urologic Clinics of North America*, 22(3):481–85 (1995).
Romanzi, L.J., et al., "Preliminary Assessment of The Incontinent Woman," *Urologic Clinics of North America*, 22(3):513–20 (1995).
Trockman, B.A., et al., "Surgical Treatment of Intrinsic Urethral Dysfunction : Injectables (Fat)," *Urologic Clinics of North America*, 22(3):665–71 (1995).
Smack, D.P., et al., "Keratin and Keratinization," *Journal of the American Academy of Dermatology*, 30(1):85–98 (1994).
McGuire, E.J., "Injection Therapy for Urinary Incontinence," *Current Surgical Techniques in Urology*, 7(3):1–7 (1994).

Frey, P., et al., "Endoscopic Subureteral Collagen Injection for the Treatment of Vesicoureteral Reflux in Infants and Children," *The Journal of Urology*, 154:804–807 (1995).
Lipsky, H., "Endoscopic Treatment of Vesicoureteral Reflux With Collagen," *Pediatr. Surg. Int.*, 6:301–03 (1991).
Dodat, H., et al., "Treatment of Vesicoureteral Reflux in Children by Endoscopic Injection of Teflon," *Pediatr. Surg. Int.*, 6:273–76 (1991).
O'Donnell, B., et al., "Endoscopic Management of Vesicoureteral Reflux," *Dialogues in Pediatric Urology*, 14(2):1–8 (1991).
Atala, A., et al., "Management of Primary Vesicoureteral Reflux," *Infections in Urology*, 39–43 (1990).
McGuire, E.J., et al., "Surgical Treatment of Intrinsic Urethral Dysfunction," *Urologic Clinics of North America*, 22(3):657–64 (1995).
DeLustro, F., et al., "The Biochemistry, Biology, and Immunology of Injectable Collagens: Contigen™ Bard® Collagen Implant in Treatment of Urinary Incontinence," *Pediatr. Surg. Int.*, 6:245–51 (1991).
Winters, J.C., et al., "Periurethral Injection of Collagen in the Treatment of Intrinsic Sphincteric Deficiency in the Female Patient," *Urologic Clinics of North America*, 22(3):673–78 (1995).
Wein, A.J., "Pharmacology of Incontinence," *Urologic Clinics of North America*, 22(3):557–77 (1995).
Bourcier, A.P., "Nonsurgical Therapy for Stress Incontinence," *Urologic Clinics of North America*, 22(3):613–27 (1995).
"Skin Test for Contingen® Bard® Collagen Implant" Bard Brochure (1993).
"Contigen® Bard® Collagen Implant" Bard Brochure (1993).
"Contigen® Bard® Collagen Implant" Bard Brochure pp. 1–14 (1993).

Primary Examiner—Cecilia J. Tsang
Assistant Examiner—Jennifer Harle
Attorney, Agent, or Firm—Nixon, Hargrave, Devans & Doyle

[57] ABSTRACT

The present invention relates to a method of augmenting soft tissue in a mammal which includes injecting keratin into the soft tissue. The method of the present invention may be used to treat incontinence and vesicoureteral reflux.

38 Claims, 2 Drawing Sheets

METHOD OF AUGMENTING SOFT TISSUE IN MAMMALS

FIELD OF THE INVENTION

This invention relates to a method of augmenting soft tissue in mammals. More particularly, the method involves injecting keratin into the soft tissue of the mammal to augment the tissue.

BACKGROUND OF THE INVENTION

Urinary incontinence (the involuntary loss of urine) is a significant clinical problem affecting roughly 10 million Americans. The failure to store urine properly typically is caused by a malfunctioning bladder or urethra. Some of the most severe cases of both male and female incontinence are those resulting from a poor or nonfunctioning bladder mechanism. Further, incontinence may be caused by a lack of anatomic support of the urethra allowing it to move out of the abdominal cavity or by an intrinsic deficiency of the urethral closure mechanism. Typically, incontinence results when pressure is exerted on the abdominal cavity. For example, a normal urethra will not leak at any physiologic abdominal pressure, while in individuals suffering from incontinence, leakage may be produced by coughing or straining. Thus, proper treatment of urinary incontinence is directed towards methods of achieved increased urethral resistance to changes in abdominal pressure.

Collagen injections have been studied to treat incontinence (Frank DeLustro, et al., "The Biochemistry, Biology, and Immunology of Injectable Collagens: Contigen™ Bard® Collagen Implant in Treatment of Urinary Incontinence," *Pediatric Surgery Int.*, 6:245–251 (1991) and Edward J. McGuire, M.D., "Injection Therapy for Urinary Incontinence," in *Current Surgical Techniques in Urology* (Carl A. Olsson eds.), 7(3):2–7 (1994), which are hereby incorporated by reference). The collagen is injected into urethral tissue, such as the urinary sphincter, to increase resistance to the flow of urine. This method suffers, however, from serious limitations. The collagen is water soluble and, thus, is absorbed by the body, so repeated treatments are necessary. This makes the cost of the collagen treatments prohibitive. In addition, some patients develop allergic reactions to collagen treatment. These reactions include rashes, swelling, erythema, and anaphylactic shock.

Collagen injections have also been utilized to augment other tissue, such as lip tissue to provide the lips with a fuller appearance. However, this procedure has the same limitations as when collagen is used for treatment of incontinence (i.e., prohibitively high cost, absorption of collagen by the body, and allergic reactions to the treatment).

Vesicourethral reflux ("VUR") is a major cause of morbidity in children. VUR is the condition in which bladder urine flows back to the ureter and, in most cases, the renal pelvis and calyces. Primary reflux results from a congenital incompetence of the ureterovesical junction. Secondary reflux results from neurogenic bladder dysfunction or bladder outlet obstruction.

In normal anatomy, the ureter enters the luminal side of the detrusor muscle and travels between the detrusor and the mucosa, lining the bladder in an intramural tunnel. As the bladder fills, there is an increase in intravesical pressure, compressing the ureteral lumen between the detrusor muscle and the bladder mucosa. This causes ureteral lumen closure, preventing reflux. An adequate length of the intramural portion of the ureter, relative to its diameter, is the most important factor in preventing reflux. At least a 4-to-1 ratio of tunnel length to ureteral diameter is necessary to prevent reflux (Paquin, A. J. Jr., "Ureterovesical Anastomosis: The Description and Evaluation of a Technique," *J. Urol*, 82:573 (1959), which is hereby incorporated by reference).

Configuration of the ureteral orifice within the bladder is also related to reflux. A cone-shaped ureteral orifice is normal. Other configurations include stadium, horseshoe, and golf hole. Respectively, these configurations represent an increasing level of association with reflux (Lyon, R. P., et al., "The Ureteral Orifice: Its Configuration and Competency," *J. Urol*, 102:504 (1969), which is hereby incorporated by reference).

Reflux of infected urine to the kidney may lead to pyelonephritis and irreversible renal scarring. Long term effects of renal scarring include hypertension and renal failure. Treatments of VUR typically relate to providing the ureter with strong support by the detrusor muscle and/or modifying the morphology of the ureter orifice.

Treatment of VUR has centered recently on the endoscopic injection of bulking agents into the bladder or ureter to provide support to the ureter and/or modify the morphology of the ureter orifice. Injection of bovine collagen into the submucosal region was described in H. Lipsky, "Endoscopic Treatment of Vesicoureteral Reflux with Collagen," *Pediatric Surgery Int.*, 6:301–303 (1991), which is hereby incorporated by reference. This method is not completely satisfactory, however, because collagen is water soluble and thus loses implant volume over time as the collagen is absorbed by the body. In humans undergoing subdermal injections, the collagen injection lost volume by twelve months. (Douglas A. Canning, M.D., "New Implants for Endoscopic Correction in the Nineties and Beyond in Endoscopic Management of Vesicoureteral Reflux," *Dialogues in Pediatric Urology*, 14(2):6–8 (1991), which is hereby incorporated by reference). The patient, therefore, must undergo repeated treatments to prevent reoccurrence of VUR. Further, collagen is prohibitively expensive, especially when repeated treatments are necessary. In addition, allergic reactions to collagen, such as rashes, swelling, erythema, and anaphylactic shock may result.

An alternative treatment is the endoscopic injection of Teflon® to treat vesicoureteral reflux. The Teflon® is injected under the refluxing orifices to provide support to the ureter. This method is not completely satisfactory, however, because the long term effects of Teflon® are unknown. Animal experiments in primates have shown that Teflon® particles may migrate into the lymph nodes, lung, or brain (Malizia, et al., "Migration and Granulomatous Reaction After Subureteric Injection of Teflon Paste in Primates," in Endoscopic Treatment of Vesicoureteric Reflux in Children, *J. Urol.* (Schulman CC eds.), 138:950–52 (1987), which is hereby incorporated by reference). Teflon® may also cause granulomatous reactions. In addition, a possible carcinogenic effect of Teflon® has been discussed (H. Lipsky, "Endoscopic Treatment of Vesicoureteral Reflux with Collagen," *Pediatric Surgery Int.*, 6:301–303 (1991)).

The present invention is directed to overcoming the deficiencies in prior treatments of these conditions.

SUMMARY OF THE INVENTION

The present invention relates to a method of augmenting soft tissue in a mammal which includes injecting keratin into the soft tissue.

Another aspect of the present invention relates to a method of treating incontinence in a mammal which includes injecting keratin into the mammal's urethral or bladder tissue to augment that tissue and to treat incontinence.

Yet another aspect of the present invention relates to a method of treating vesicoureteral reflux in a mammal which includes injecting keratin into the mammal's bladder or ureteral tissue to augment that tissue and to reduce vesicoureteral reflux.

The method of the present invention provides advantages not attainable with the previously-described methods. In particular, the keratin is not soluble, so it will not be absorbed by the body. As a result, there is no need for repeated treatments which significantly reduces the cost of patient treatment. Further, keratin can be used in those patients allergic to the collagen substance.

DETAILED DESCRIPTION OF THE INVENTION

Figure 1:
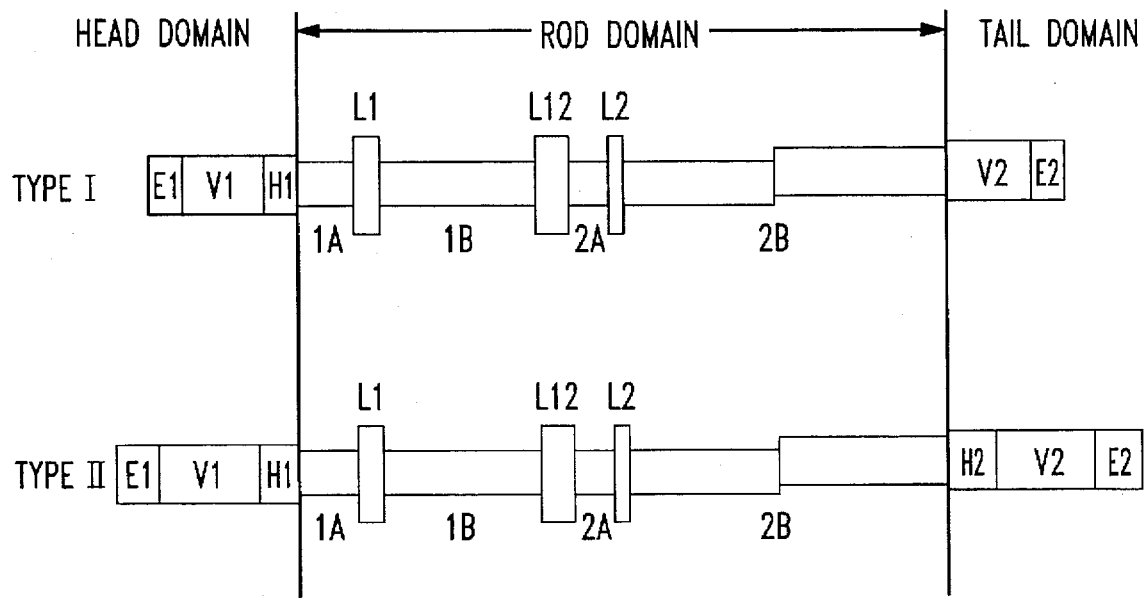
FIG. 1 is a diagrammatic representation of keratin polypeptides.

The present invention relates to a method of augmenting soft tissue in a mammal which includes injecting keratin into the soft tissue.

The cytoskeleton of all mammalian cells is composed of three filament systems. These are the microfilaments (6 nm), intermediate filaments (8 to 10 nm), and microtubules (25 nm). The keratins are members of the intermediate filament ("IF") family. All IF proteins possess a similar protein structural organization that consists of a central α-helical rod domain of conserved secondary structure flanked by distinct amino- and carboxyl-terminal end domains. The structure of these three domains is the basis for classification of the IF into six different sequence types. The keratins are subdivided into the acidic type I and the neutral-basic type II IFs. Vimentin, desmin, glial fibrillary acidic protein, and peripherin are all type III IFs. The type IV IFs consist of the neurofilaments (heavy chain, light chain, and medium chain) and α-internexin. The type V IFs consist of the nuclear lamins (A, B1 and B2, and C). Nestin is the only member of the type VI IF group. A listing of the IFs are shown below in Table I.

TABLE I

| | Intermediate filaments | | | |
|---|---|---|---|---|
| Type | Name | Origin | No. | Molecular weight (kd) |
| I | Acidic keratins | All epithelia | 15 | 40–60 |
| II | Neutral-basic keratins | All epithelia | 15 | 50–70 |
| III | Vimentin | Mesenchymal cells | 1 | 53 |
| | Desmin | Myogenic cells | 1 | 52 |
| | Glial fibrillary acidic protein | Glial cells, astrocytes | 1 | 51 |
| | Peripherin | Neurons | 1 | 52 |
| IV | Neurofilaments | Neurons | 3 | 60–150 |
| | α-Internexin | Prenatal Neurons | 1 | 57 |
| V | Nuclear lamins | Nuclear lamina of | 4 | 60–70 |

TABLE I-continued

| | Intermediate filaments | | | |
|---|---|---|---|---|
| Type | Name | Origin | No. | Molecular weight (kd) |
| VI | Nestin | all eukaryotes Embryonal, neuroepithelial stem cells | 1 | 200 |

Keratins are the largest IF group with at least 30 different protein chains, consisting of roughly 20 epithelial keratins and 10 hair keratins. Several classification schemes have been introduced for the epithelial group of keratins. The classification detailed in Moll, et al., "The Catalog of Human Cytokeratins: Patterns of Expression in Normal Epithelia, Tumors and Cultured Cells," Cell, 31:11–24 (1982) and Moll, et al., "Identification of Protein IT of the Intestinal Cytoskeleton as a Novel Type I Cytokeratin with Unusual Properties and Expression Patterns," J. Cell Bio., 111:567–80 (1990), which are hereby incorporated by reference, is most widely used. It is based on dividing the different keratins according to Molecular Weight ("MW") and isoelectric points with the assignment of a number to each keratin (as shown in Table II below).

TABLE II

| | Epithelial keratins | | | |
|---|---|---|---|---|
| | Moll No. | Molecular weight (kd) | Pairing | Marker for |
| Type I: Acidic | K10 | 56.5 | K1, K2 | Skin (terminal) differentiation, keratinization, suprabasal keratinocytes |
| | K12 | 55 | K3 | Corneal differentiation |
| | K13 | 51 | K4 | Esophageal differentiation, nonkeratinizing "wet" epithelia |
| | K14, K15 | 50, 50' | K5 | Basal keratinocytes, stratified epithelia only |
| | K16 | 48 | K6 | Hyperproliferation — associated keratinocytes, palms/soles |
| | K17 | 46 | K7 | Stratified and simple epithelia |
| | K18 | 45 | K8 | Simple epithelia |
| | K19 | 40 | K8 | Simple epithelia |
| | K20 | 46 | K8 | Intestinal epithelia |
| Type II: Neutral-basic | K1, K2 | 65–67 | K10 | Skin (terminal) differentiation, keratinization, suprabasal keratinocytes |
| | K3 | 64 | K12 | Corneal differentiation |
| | K4 | 59 | K13 | Esophageal differentiation, nonkeratinizing "wet" epithelia |
| | K5 | 58 | K14, K15 | Basal keratinocytes, stratified epithelia only |
| | K6 | 56 | K16 | Hyperproliferation — associated keratinocytes, |

TABLE II-continued

Epithelial keratins

| Moll No. | Molecular weight (kd) | Pairing | Marker for |
|---|---|---|---|
| K7 | 54 | K17 | palms/soles Stratified and simple epithelia |
| K8 | 52 | K18, K19, K20 | Simple epithelia |
| K9 | 64 | NK | Palms/soles |

NK = Not Known

Characteristics of type I (acidic) epithelial keratins are acidic isoelectric points. Members consist of Moll Nos. K10 through K20 and MW range of 40 to 56.5 kd. Features of type II (neutral-basic) epithelial keratins are neutral-basic isoelectric points. Members consist of Moll Nos. K1 through K9 and MW range of 52 to 67 kd.

Keratin polypeptides are the primary building block of keratin intermediate filaments ("KIF") (also referred to as tonofilaments). On the basis of protein structural predictions, keratin polypeptides have a central rod domain consisting of highly conserved sequences containing approximately 310 amino acids with four largely α-helical segments referred to as 1A, 1B, 2A, and 2B. These segments are arranged as heptad repeats of the form $(a-b-c-d-e-f-g)_n$, where the "a" and "d" are generally hydrophobic residues. Interrupting the α-helical segments are three nonhelical linker sequences (L1, L12, and L2) that presumably confer some flexibility to the rod.

The central rod domain is flanked by an amino-terminal "head" domain and a carboxyl-terminal "tail" domain. The nonhelical "head" and "tail" domains have also been divided into subdomains based on sequence comparisons to all other IFs. These include subdomains with a high degree of homology to each other within the type I and type II keratin polypeptide subfamilies (H subdomains), subdomains that consist of variable numbers of quasi peptide repeats (V subdomains), and subdomains that are highly charged (E subdomains). For the type I keratin polypeptides, the "head" domain consists of E1, V1, and E1, whereas the "tail" domain consists of V2 and E2. For the type II keratin polypeptides, the "head" domain also consists of E1, V1, and H1, whereas the "tail" domain constitutes H2, V2, and E2. A diagrammatic representation of type I and type II keratin polypeptides is shown in FIG. 1.

The functional properties of the central rod, "head," and "tail" domains are currently being studied. The central rod domain appears to specify the way that keratin polypeptides interact during KIF formation. However, there are several indications that at least some "head" and "tail" domain sequences are equally necessary for proper KIF assembly and stabilization in vitro and in vivo. In addition, the end domains seem to confer the specific functional characteristics of the KIF network required by a particular cell type. For example, protein structural analysis and nuclear magnetic resonance studies suggest that the glycine-rich "head" and "tail" domains of the keratins K1 and K10 are highly flexible and are likely to interact with other similar or related structures (e.g., loricrin). These sequences are proposed to form a protein structural motif, termed glycine loop by Steinert, et al., "Glycine Loops in Proteins: Their Occurrence in Certain Intermediate Filament Chains, Loricrins and Single-Stranded RNA Binding Proteins," Int. J. Biol. Macromol, 13:130–39 (1991), which is hereby incorporated by reference, that may contribute to the flexibility of the epidermis (Conway, et al., "intermediate Filament Structure: 3. Analysis of Sequence Homologies," Int. J. Biol. Macromol, 10:79–98 (1988); Letai, et al., "Do the Ends Justify the Means? Proline Mutations at the Ends of the Keratin Coiled-Coil Rod Segment are More Disruptive Than Internal Mutation," J. Cell Biol., 116:181–95 (1992); Lu, et al., "Retrovirus-mediated Transgenic Keratin Expression in Cultured Fibroblasts: Specific Domain Functions in Keratin Stabilization and Filament Formation," Cell, 62:681–96 (1990); Steinert, P.M., "The Two-Chain Coiled-Coil Molecule of Native Epidermal Keratin Intermediate Filaments is a Type I Type II Heterodimer," J. Biol. Chem., 265:8766–74 (1990); Steinert, et al., "Intermediate Filament Dynamics," Cell, 60:521–23 (1990); Ibers, et al., "Expression of Mutant Keratin cDNAs in Epithelial Cells Reveals Possible Mechanisms for Initiation and Assembly of Intermediate Filaments," J. Cell Biol., 108:1477–93 (1989); Coulombe, et al., "Deletions in Epidermal Keratins Leading to Alterations in Filament Organization In Vivo and in Intermediate Filament Assembly in Vitro," J. Cell Biol., 111:3049–64 (1990); Hatzfeld, et al., "The Coiled Coil of In Vitro Assembly Keratin Filaments is a Heterodimer of Type I and II Keratins: Use of Site-Specific Mutagenesis and Recombinant Protein Expression," J. Cell Biol., 110:1199–210 (1990); Parry, et al., "Intermediate Filament Structure," Curr. Opin. Cell Biol., 4:94–98 (1992); Steinert, et al., "Glycine Loops in Proteins: Their Occurrence in Certain Intermediate Filament Chains, Loricrins and Single-Stranded RNA Binding Proteins," Int. J. Biol. Macromol, 13:130–39 (1991); Aebi, et al., "Unifying Principles in Intermediate Filament (IF) Structure and Assembly," Protoplasma, 145:73–81 (1988); Mack, et al., "Solid State NMR Studies on the Dynamic Structure of Mouse Epidermal Keratin Filaments," Biochemistry, 27:5418–26 (1988); Kaufmann, et al., "Intermediate Filament Forming Ability of Desmin Derivatives Lacking Either the Amino-Terminal 67 or the Carboxyl-Terminal 27 Residues," J. Mol. Biol., 185:733–42 (1985); Shoeman, et al., "Intermediate Filament Assembly and Stability In Vitro: Effect and Implications of the Removal of Head and Tail Domains of Vimentin by the Human Immunodeficiency Virus Type I Protease," Cell Biol. Int. Rep., 14:583–94 (1990); Hatzfeld, et al., "Tailless Keratins Assemble into Regular Intermediate Filaments In Vitro," J. Cell Sci., 97:317–24 (1990); and Albers, et al., "The Expression of Mutant Epidermal Keratin cDNAs Transfected in Simple Epithelial and Squamous Cell Carcinoma Lines," J. Cell Biol., 105:791–806 (1987), which are hereby incorporated by reference).

Loricrin is rich in glycine, serine, and cysteine and possesses a MW of 26 kd. It is insoluble and initially accumulates in keratohyaline granules. Sequencing reveals a unique composition with several long regions rich in glycine that are separated and bounded by short glutamine-and glutamine/lysine-rich segments. The glycine-rich sequences are predicted to be highly flexible and capable of "glycine loop" formation, analogous to the "glycine loops" postulated for the V1 and V2 regions of several keratin polypeptides (Steinert, et al., "Glycine Loops in Proteins: Their Occurrence in Certain Intermediate Filament Chains, Loricrins and Single-Stranded RNA Binding Proteins," Int. J. Biol. Macromol, 13:130–39 (1991); Korge, et al., "Extensive Size Polymorphism of Human Keratin 10 Chain Resides in the Carboxyl-Terminal V2-Subdomain Due to Variable Number and Sizes of Glycine Loops," Proc. Natl. Acad. Sci U.S.A., 89:910–14 (1992); and Korge, et al., "The Two Size Alleles of Human Keratin 1 are Due to a Deletion in the Glycine-Rich Carboxyl-Terminal V2 Subdomain," J. Invest.

Figure 2:
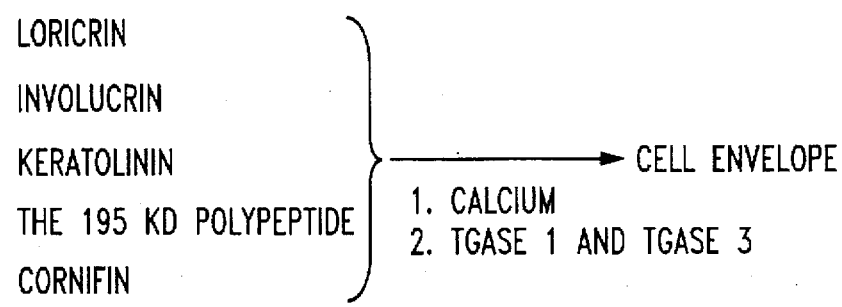
FIG. 2 is a representation of cell envelope formation.

Dermatol., 99:697–702 (1992), which are hereby incorporated by reference). These sequences may function to confer flexibility and extensibility to the epidermis and promote nonspecific interaction between KIFs and CE. Loricrin incorporation into the cell envelope or cornified envelope ("CE") by epidermal transglutaminases has been documented in vivo, by identification of loricrin polypeptides directly cross-linked to the CE by isodipeptide bonds (FIG. 2) (Mehrel, et al., "Identification of a Major Keratinocyte Cell Envelope Protein, Loricrin," Cell, 61:1103–12 (1990); Hohl, D., "Cornified Cell Envelope," Dermatologica, 180:201–11 (1990); Hohl, et al., "Transcription of the Human Loricrin Gene In Vitro is Induced by Calcium and Cell Density and Suppressed by Retinoic Acid," J. Invest. Dermatol., 96:414–18 (1991); Yoneda, et al., "The Human Loricrin Gene," J. Biol. Chem., 267:18060–66 (1992); and Hohl, et al., "Characterization of Human Loricrin: Structure and Function of a New Class of Epidermal Cell Envelope Proteins," J. Biol. Chem., 266:6626–36 (1991), which are hereby incorporated by reference).

Involucrin possesses a MW of 68 kd and contains 45.8 glutamine residues per 100 amino acids. Despite the availability of 150 glutamine residues for formation of $\epsilon$-($\gamma$-glutamyl)-lysine isopeptide cross-links, epidermal transglutaminases in vitro preferentially interact with a single glutamine (residue 496), located 89 residues form the C-terminal end of the involucrin polypeptide. In epidermal cell cultures, this protein is synthesized in the suprabasal compartment and found in abundance (as a soluble fraction) in the keratinocyte cytoplasm. Crosslinking renders the cytosolic involucrin insoluble before proposed incorporation in to the CE (FIG. 2) (Hohl, D., "Cornified Cell Envelope," Dermatologica, 180:201–11 (1990); Baden, et al., "A New Class of Soluble Basic Protein Precursors of the Cornified Envelope of Mammalian Epidermis," Biochem. Biophys. Acta, 925:63–73 (1987); Etoh, et al., "Involucrin Acts as a Transglutaminase Substrate at Multiple Sites," Biochem. Biophys. Res. Commun., 136:51–56 (1986); and Simon, et al., "The Glutamine Residues Reactive in Transglutaminase-Catalyzed Cross-Linking of Involucrin," J. Biol. Chem., 263:18093–98 (1988), which are hereby incorporated by reference).

Keratolinin (cystatin A) is constructed from 6 kd protein subunits containing 13.5 glutamine residues per 100 amino acids. After synthesis, these subunits readily polymerize within the cytoplasm to form the 36 kd polypeptide, which in vitro serves as a substrate for epidermal transglutaminases. Cross-linked keratolinin decorates the cell periphery in the stratum corneum and is proposed to be incorporated into the CE. Keratolinin synthesis is confined to the suprabasal compartment and is a marker for terminal keratinocyte differentiation (FIG. 2) (Hohl, D., "Cornified Cell Envelope," Dermatologica, 180:201–11 (1990); Zettergren, et al., "Keratolinin: The Soluble Substrate of Epidermal Transglutaminase from the Human and Bovine Tissue," Proc. Natl. Acad. Sci. U.S.A., 81:238–42 (1984); Passavant, et al., "The Identification of cDNA Clones Coding for a Protein Which Reacts with Anti-Keratolinin [Abstract]," J. Invest. Dermatol., 92:497 (1989); and Hawley-Nelson, et al., "Molecular Cloning of Mouse Epidermal Cystatin A and Detection of Regulated Expression in Differentiation and Tumorigenesis," Mol. Carcinog., 1:202–11 (1988), which are hereby incorporated by reference).

The 195 kd polypeptide is not as well characterized as the other CE proteins. In the lower suprabasal compartment, this polypeptide exists as a soluble fraction in the cytoplasm of keratinocytes. During keratinocyte terminal differentiation, the 195 kd protein becomes progressively deposited in an insoluble form at the cell periphery, suggesting incorporation into the CE. Interactions with epidermal transglutaminases remain uncharacterized (Ma, et al., "Differentiation-Dependent Changes in the Solubility of a 195-kD Protein in Human Epidermal Keratinocytes, J. Cell Biol., 103:41–48 (1986), which is hereby incorporated by reference). Finally, one other proposed component of the CE, cornifin (small proline-rich protein), has recently been identified and is currently being studied (FIG. 2) (Hohl, D., "Cornified Cell Envelope," Dermatologica, 180:201–11 (1990) and Marvin, et al., "Cornifin, a Cross-Linked Envelope Purcursor in Keratinocytes that is Down-Regulated by Retinoids," Proc. Natl. Acad. Sci. U.S.A., 89:11026–30 (1992), which are hereby incorporated by reference).

The basal cell layer is the only place in which keratinocytes can divide and proliferate. KIFs (tonofilaments) in this compartment are predominantly composed of the keratins K5 and K14. On entering the spinous cell layer, keratinocytes start down the one-way path of terminal differentiation increasing in size and metabolic activity. During this phase, the translation of messenger RNAs encoding the keratins K5 and K14 is abruptly shut down, whereas synthesis of K1 and K10 is upregulated. These keratin polypeptides readily polymerize in the cytoplasm to form KIFs, which then aggregate into bundles. In addition, keratohyaline granule proteins and CE proteins are synthesized. In the granular cell layer, the keratohyaline granules appear, KIFs continue to aggregate in ever larger bundles, metabolic activity wanes, and the keratinocytes begin to lose their cytoplasmic organelles. Profilaggrin is released from keratohyaline granules and undergoes proteolysis and dephosphorylation to form filaggrin. Filaggrin then acts as a matrix protein and establishes a precise, parallel alignment of the already present KIFs, densely packing them into bundles with resultant formation of macrofibrils. Shortly thereafter, the permeability of the keratinocyte plasma membrane increases allowing a calcium ion influx that, together with the release of sequestered calcium from degenerating cellular organelles and bound calcium from calcium-binding proteins, may activate the calcium-dependent, epidermal transglutaminases. These enzymes catalyze the irreversible cross-linking of loricrin, involucrin, keratolinin, the 195 kd protein, and cornifin to form the CE.

All keratinocytes present in the cornified layer are dead. In the lower stratum corneum they are composed of a plasma membrane surrounding an impervious CE packed with keratin macrofibrils. In the upper stratum corneum, the plasma membrane (along with its desmosomes) becomes discontinuous and is replaced by the insoluble CE. This cross-linked structure then serves as a shield against external environmental hazards (Cooper, et al., "Classification of Human Epithelia and their Neoplasms Using Monoclonal Antibodies to Keratins: Strategies, Applications, and Limitations," Lab. Invest., 52:243–56 (1985); Lever, et al., "Histopathology of the Skin," 7th ed. New York: Lippincott, 9–15, 66–67, 77–79 (1991); Eckert, R. L., "Structure, Function, and Differentiation of the Keratinocyte," Physiol. Rev., 69:1316–46 (1989); Hohl, D., "Cornified Cell Envelope," Dermatologica, 180:201–11 (1990); Hohl, et al., "Transcription of the Human Loricrin Gene In Vitro is Induced by Calcium and Cell Density and Suppressed by Retinoic Acid," J. Invest. Dermatol., 96:414–18 (1991); and Polakowska, et al., "The Cell Envelope and Transglutaminases. In Goldsmith LA, ed. Histology, Biochemistry and Molecular Biology of the Skin. New York Oxford University Press, 168–120 (1991), which are hereby incorporated by reference).

The keratins involved in formation of hair and nails are a combination of the epithelial keratins discussed above and several unique keratins specific to "hard" keratinization. These hair keratins are not as well characterized as their epithelial counterparts in terms of structure, cellular distribution within the hair follicle and nail unit, and function. Heid et al, "The Complement of Native α-Keratin Polypeptides of Hair-Forming Cells: A Subset of Eight Polypeptides that Differ from Epithelial Cytokeratins," *Differentiation*, 32:101–19 (1986) utilizing features comparable to those used by Moll et al., "The Catalog of Human Cytokeratins: Patterns of Expression in Normal Epithelia, Tumors and Cultured Cells," *Cell*, 31:11–24 (1982) divide these eight major (Ha1 through 4 and Hb1 through 4) and two minor (Hax and Hbx) keratins into two subfamilies. (Heid, et al., "Patterns of Expression of Trichocytic and Epithelial Cytokeratins in Mammalian Tissues. I. Human and Bovine Hair Follicles," *Differentiation*, 37:137–57 (1988); Moll, et al., "Patterns of Expression of Trichocytic and Epithelial Cytokeratins in Diverse Mammalian Tissues. III. Hair and Nail Formation During Human Fetal Development," *Differentiation*, 39:167–84 (1988); Moll, et al., "Changes in the Pattern of Cytokeratin Polypeptides in Epidermis and Hair Follicles During Skin Development in Human Fetuses," *Differentiation*, 23:170–78 (1982); Heid, et al., "Patterns of Expression of Trichocytic and Epithelial Cytokeratins in Mammalian Tissues, II. Concomitant and Mutually Exclusive Synthesis of Trichocytic and Epithelial Cytokeratins in Diverse Human and Bovine Tissues (Hair Follicle, Nail Bed and Matrix, Lingual Papilla, Thymic Reticulum)," *Differentiation*, 37:215–30 (1988); Stark, et al., "Keratins of the Human Hair Follicle: "Hyperproliferative" Keratins Consistently Expressed in Outer Root Sheath Cells In Vivo and In Vitro," *Differentiation*, 35:236–48 (1987); and Lynch, et al., "Acidic and Basic Hair/Nail ("Hard") Keratins: Their Colocalization in Upper Cortical and Cuticle Cells of the Human Hair Follicle and Their Relationship to "Soft" Keratins," *J. Cell Biol.*, 103:2593–606 (1986), which are hereby incorporated by reference). These two subfamilies are (1) type I (acidic) hair keratins (acidic isoelectric points, members consists of Ha1–4 and Hax, MW range of 42 to 54.5 kd) and (2) type II (neutral-basic) hair keratins (neutral-basic isoelectric points, members consist of Hb1–4 and Hbx, and MW range of 56.5 to 64 kd).

These 10 keratins appear to be expressed in the shaft portion of the hair follicle and its surrounding cuticle, in nail-forming cells, in filiform papillae of the tongue, and in the thymic epithelium.

The keratin used in the methods of the present invention may be any of the keratins discussed above. For example, the keratin used in the methods can be any of the epithelial keratins, any of the hair keratins, or any keratin fragment including the head domains, tail domains, rod domains and combinations of these domains. Further, the keratin fragment may be from the L subdomains, H subdomains, V subdomains, E subdomains, or combinations thereof. The keratin may be derived from keratin collected from any number of human or animal sources. Keratin may be obtained from human skin, hair, or fingernails or animal feathers, bristles, skin, hooves, hair, wool, or horns. The keratin may also be derived synthetically. Typically, the keratin used in the present invention is provided by Freeman Industries (Tuckahoe, N.Y.).

The keratin is injected into the soft tissue of a mammal to augment the soft tissue. It is especially desirable to augment the lip tissue, bladder tissue, urethral tissue, esophagus tissue, vocal cord tissue and skin tissue of the mammal. For example, the keratin may be injected into the lower esophageal sphincter of a mammal to treat gastro-esophageal reflux, or be injected into the vocal cords of a mammal for the treatment of paralyzed vocal cords. Further, keratin may be injected into the skin tissue to augment the skin tissue to repair or correct congenital anomalies, acquired defects, or cosmetic defects. Examples of such conditions are congenital anomalies such as hemifacial microsomia, malar and zygomatic hypoplasia, unilateral mammary hypoplasia, pectus excavatum, pectoralis agenesis (Poland's anomaly) and velopharyngeal incompetence secondary to cleft palate repair or submucous cleft palate (as a retropharyngeal implant); acquired defects (post traumatic, post surgical, post infectious) such as depressed scars, subcutaneous atrophy (e.g., secondary to discoid lupis erythematosis), keratotic lesions, enophthalmos in the unucleated eye (also superior sulcus syndrome), ache pitting of the face, linear scleroderma with subcutaneous atrophy, saddle-nose deformity, Romberg's disease and unilateral vocal cord paralysis; and cosmetic defects such as glabellar frown lines, deep nasolabial creases, circum-oral geographical wrinkles, sunken cheeks and mammary hypoplasia. One embodiment of the present invention is to inject the keratin into the lip tissue of a mammal to augment the lips, giving the lips a fuller, more aesthetically pleasing appearance.

Preferably the keratin is mixed with a liquid agent to form a paste prior to injection. The composition typically contains from 25 to 75 wt. % keratin and 75 wt. % to 25 wt. % liquid agent. It is more preferable for the composition to contain 40 to 60 wt. % keratin, with 50 wt. % being most preferred, and the remainder liquid agent. Up to 30 cc of the keratin composition is injected into the desired tissue to augment that tissue and to achieve the desired result.

In another method of the invention, the keratin is injected into the soft tissue of the mammal to treat incontinence. The method is achieved by injecting keratin into the bladder or urethra tissue. Preferably the keratin is first mixed with a liquid agent to form a paste, as described above. Up to 30 cc of this composition is injected into the submucosal tissue of the urethra and/or the bladder neck and periurethral tissues. Control of the amount of keratin injected is maintained by continuous endoscopic inspection of the lumen of the urethra. The keratin is injected until the tissue bulk increase results in urethral closure. This results in increased resistance of the urethra Go the abdominal pressures which result in incontinence.

Figure 3A:
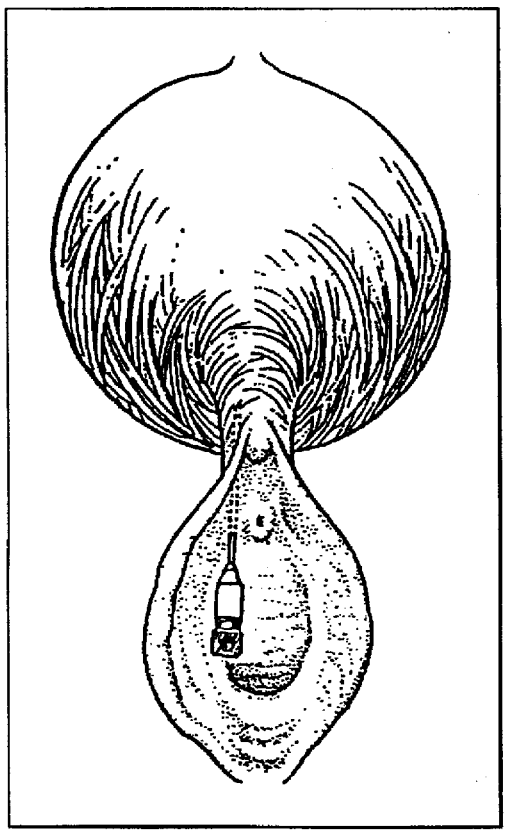
FIG. 3A is a first representation of the procedure of one embodiment of the present invention.
Figure 4:
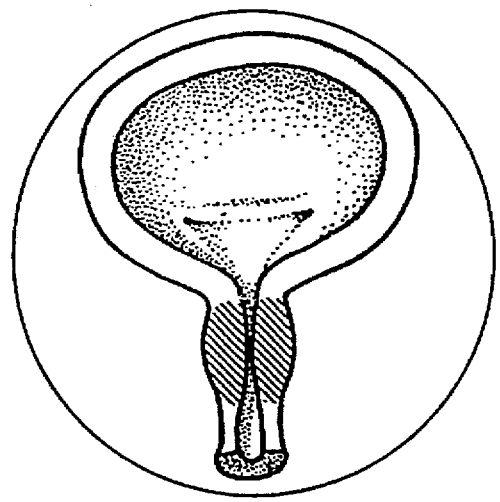
FIG. 4 is a diagrammatic representation of an urethra treated by the procedure shown in FIGS. 3A and 3B.
Figure 3B:
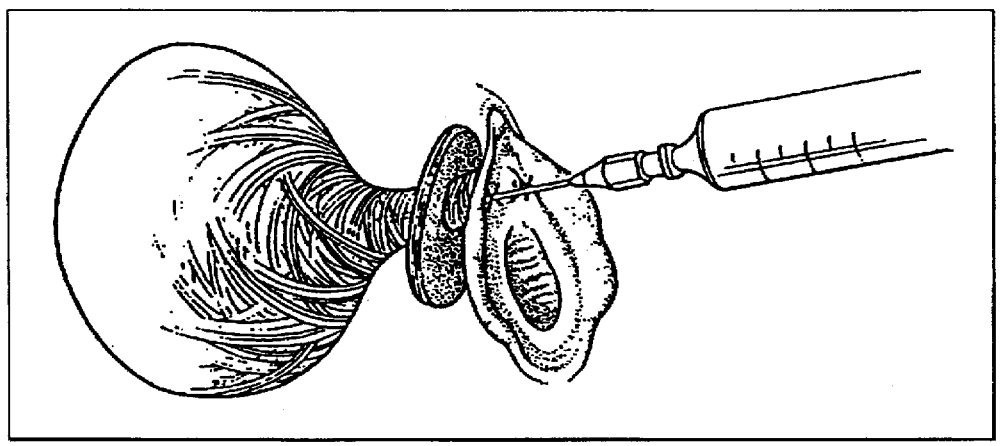
FIG. 3B is a second representation of the procedure shown in FIG. 3A.

Preferably, to treat incontinence in women the injection is done via the paraurethral route or the transurethral route. In the paraurethral route, a 22-gauge spinal needle is advanced in an oblique plane, beginning at 10 and 2 o'clock on either side and moving forward along the axis of the urethra inclined slightly toward the lumen, while the proximal urethra is visualized endoscopically. As the needle approaches the urethral wall, the entire side of the urethra will move along with it. When the needle approaches the area where the injection should be delivered (FIGS. 3A and 3B), only local motion of the urethral wall will be seen with movement of the needle. At this point, the injection is done slowly, to allow the tissue to accommodate the material. In some cases, it is necessary to inject keratin circumferentially at three or four spots around the urethra, but typically one injection on each side will be sufficient. The objective is to deform the mucosa of the urethra to the midline (FIG. 4).

For a transurethral route, the needle is introduced into the submucosal plane under direct endoscopic vision. All other aspects of the procedure are identical to that discussed for the paraurethral route.

To treat incontinence in men, the procedure is done in a similar manner. The tissue in males is less receptive to injection, and the length of urethra into which the material can be injected is shorter. Thus incontinence in men is much more difficult to treat. Therefore, typically, additional injection sites may be necessary to gain full closure of the urethra.

In another aspect of the invention, keratin is injected into the bladder or ureter tissue to reduce vesicourethral reflux. In this method, the keratin is preferably mixed with a liquid agent to form a paste, as described above. Up to 1.2 cc of the keratin composition is injected into the bladder or the ureteral tissue to augment the tissue. Ideally, only 0.2 to 0.7 cc is required. Typically, the composition is injected into suburetic tissue, such as the mucosa of the ureter at the ureterovesical junction or into the mucosa of the ureteral lumen. The bulking of the tissue provides strong support for the detrusor muscle and/or modifies the morphology of the ureter orifice such that vesicourethral reflux is reduced.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of augmenting soft tissue in mammals comprising:

injecting keratin into the soft tissue, wherein the soft tissue is bladder tissue or urethral tissue.

2. A method according to claim 1, wherein the soft tissue is bladder tissue.

3. A method according to claim 1, wherein the soft tissue is urethral tissue.

4. A method according to claim 1, wherein the keratin is injected as a composition further comprising:

a liquid agent mixed with the keratin to form a paste.

5. A method according to claim 4, wherein the composition comprises from 25 to 75 wt. % keratin and 75 to 25 wt. % liquid agent.

6. A method according to claim 5, wherein the composition comprises from 40 to 60 wt. % keratin and from 60 to 40 wt. % liquid agent.

7. A method according to claim 4, wherein the keratin is selected from the group consisting of epithelial keratin, hair keratin, synthetic keratin, and keratin fragments.

8. A method according to claim 7, wherein the keratin is an epithelial keratin selected from the group consisting of Type I acidic keratin and Type II neutral-basic keratin.

9. A method according to claim 7, wherein the keratin is hair keratin selected from the group consisting of Type I acidic keratin and Type II neutral-basic keratin.

10. A method according to claim 7, wherein the keratin is a keratin fragment selected from the group consisting of head domains, tail domains, rod domains, and combinations of such domains.

11. A method according to claim 7, wherein the keratin is a keratin fragment selected from the group consisting of L subdomains, H subdomains, V subdomains, E subdomains, and combinations thereof.

12. A method according to claim 7, wherein the keratin is a synthetic keratin.

13. A method according to claim 7, wherein the keratin is human keratin.

14. A method of treating incontinence in a mammal comprising:

injecting keratin into the mammal's urethral or bladder tissue to augment that tissue and to reduce incontinence.

15. A method according to claim 14, wherein the keratin is injected into periurethral tissue.

16. A method according to claim 14, wherein the keratin is injected into the submucosal tissue.

17. A method according to claim 14, wherein the keratin is injected as a composition further comprising:

a liquid agent mixed with the keratin to form a paste.

18. A method according to claim 17, wherein the composition comprises from 25 to 75 wt. % keratin and from 75 to 25 wt. % liquid agent.

19. A method according to claim 18, wherein the composition comprises from 40 to 60 wt % keratin and from 60 to 40 wt. % liquid agent.

20. A method according to claim 17 wherein the keratin is selected from the group consisting of epithelial keratin, hair keratin, synthetic keratin, and keratin fragments.

21. A method according to claim 20, wherein the keratin is an epithelial keratin selected from the group consisting of Type I acidic keratin and Type II neutral-basic keratin.

22. A method according to claim 20, wherein the keratin is hair keratin selected from the group consisting of Type I acidic keratin and Type II neutral-basic keratin.

23. A method according to claim 20, wherein the keratin is a keratin fragment selected from the group consisting of head domains, tail domains, rod domains, and combinations of such domains.

24. A method according to claim 20, wherein the keratin is a keratin fragment selected from the group consisting of L subdomains, H subdomains, V subdomains, E subdomains, and combinations thereof.

25. A method according to claim 20, wherein the keratin material is a synthetic keratin.

26. A method according to claim 20, wherein the keratin is human keratin.

27. A method of treating vesicoureteral reflux in a mammal comprising:

injecting keratin into the mammal's bladder or ureter tissue to augment that tissue and to reduce vesicoureteral reflux.

28. A method according to claim 27, wherein the keratin is injected into the suburetic tissue.

29. A method according to claim 27, wherein the keratin is injected as a composition further comprising:

a liquid agent mixed with the keratin to form a paste.

30. A method according to claim 29, wherein the composition comprises from 25 to 75 wt. % keratin and from 75 to 25 wt. % liquid agent.

31. A method according to claim 30, wherein the composition comprises from 40 to 60 wt. % keratin and from 60 to 40 wt. % liquid agent.

32. A method according to claim 29, wherein the keratin is selected from the group consisting of epithelial keratin, hair keratin, synthetic keratin, and keratin fragments.

33. A method according to claim 29, wherein the keratin is an epithelial keratin, selected from the group consisting of Type I acidic keratin and Type II neutral-basic keratin.

34. A method according to claim 29, wherein the keratin is hair keratin selected from the group consisting of Type I acidic keratin and Type II neutral-basic keratin.

35. A method according to claim 29, wherein the keratin is a keratin fragment selected from the group consisting of head domain, tail domain, rod domain, and combinations of two such domains.

36. A method according to claim 29, wherein the keratin is a keratin fragment selected from the group consisting of L subdomains, H subdomains, V subdomains, E subdomains, and combinations thereof.

37. A method according to claim 29, wherein the keratin is a synthetic keratin.

38. A method according to claim 29 wherein the keratin is human keratin.

* * * * *